(12) United States Patent
Wiltberger et al.

(10) Patent No.: US 11,143,828 B2
(45) Date of Patent: Oct. 12, 2021

(54) OPTICAL SWITCH AND METHOD FOR TREATMENT OF TISSUE

(71) Applicant: IRIDEX Corporation, Mountain View, CA (US)

(72) Inventors: Michael W. Wiltberger, Santa Clara, CA (US); Dan E. Andersen, Menlo Park, CA (US); David H. Mordaunt, Los Gatos, CA (US)

(73) Assignee: IRIDEX Corporation, Mountain View, CA (US)

( * ) Notice: Subject to any disclaimer, the term of this patent is extended or adjusted under 35 U.S.C. 154(b) by 85 days.

(21) Appl. No.: 16/655,050

(22) Filed: Oct. 16, 2019

(65) Prior Publication Data

US 2020/0096714 A1 Mar. 26, 2020

Related U.S. Application Data

(63) Continuation of application No. 11/523,159, filed on Sep. 18, 2006, now Pat. No. 10,488,606.

(Continued)

(51) Int. Cl.
*A61F 9/008* (2006.01)
*A61F 9/007* (2006.01)
(Continued)

(52) U.S. Cl.
CPC ........ *G02B 6/4214* (2013.01); *A61F 9/00817* (2013.01); *G02B 26/0816* (2013.01);
(Continued)

(58) Field of Classification Search
CPC .. A61F 9/008; A61F 9/00821; A61F 9/00823; A61F 9/00727; A61F 2009/00863; A61F 2009/00897
(Continued)

(56) References Cited

U.S. PATENT DOCUMENTS 3,703,176 A 11/1972 Vassiliadis et al.
4,088,885 A 5/1978 Meslener
(Continued)

FOREIGN PATENT DOCUMENTS

WO 2002/083041 A1 10/2002
WO 2004/036705 A1 4/2004

OTHER PUBLICATIONS

AZO Optics, "Aiming Beam and Coaxial Laser Beam", Available at: https://www.azooptics.com/Article.aspx?ArticleID=782, Sep. 19, 2014, 5 pages.

(Continued)

*Primary Examiner* — John R Downey
(74) *Attorney, Agent, or Firm* — Kilpatrick Townsend & Stockton LLP (57) ABSTRACT

An optical switch incorporated in a photomedical system, and a method of treating tissue using the optical switch for creating pulsed light. A light source generates an optical beam. An aperture element includes a light-transmitting portion and a light-blocking portion. An optical element such as a mirror, prism or lens directs the optical beam to the aperture element, wherein the optical element is movable for translating the optical beam across the light-transmitting and light-blocking portions of the aperture element, or changing its angle of incidence through the aperture to produce one or more pulses of light from the optical beam. A lens focuses the one or more pulses of the optical beam onto target tissue. A controller controls the movement of the optical element to produce the one or more pulses of light.

24 Claims, 6 Drawing Sheets

Related U.S. Application Data (60) Provisional application No. 60/718,791, filed on Sep. 19, 2005.

(51) Int. Cl.
  *G02B 6/42* (2006.01)
  *G02B 26/08* (2006.01)
  *A61B 3/135* (2006.01)
  *G02B 6/26* (2006.01)

(52) U.S. Cl.
  CPC ......... *A61B 3/135* (2013.01); *A61F 9/00727* (2013.01); *A61F 2009/00863* (2013.01); *G02B 6/266* (2013.01)

(58) Field of Classification Search
  USPC .......................................... 606/4–6
  See application file for complete search history.

(56) References Cited

U.S. PATENT DOCUMENTS

| | | |
|---|---|---|
| 4,583,539 A | 4/1986 | Karlin et al. |
| 4,917,486 A | 4/1990 | Raven et al. |
| 5,065,515 A | 11/1991 | Iderosa |
| 5,300,062 A | 4/1994 | Ueno |
| 5,637,109 A | 6/1997 | Sumiya |
| 6,096,028 A | 8/2000 | Bahmanyar et al. |
| 6,099,522 A | 8/2000 | Knopp et al. |
| 6,679,876 B2 | 1/2004 | Kondo et al. |
| 6,720,524 B1 | 4/2004 | Hamada |
| 6,814,454 B2 | 11/2004 | Aziz et al. |
| 7,146,983 B1 | 12/2006 | Hohla et al. |
| 2005/0055015 A1 | 3/2005 | Buzawa |
| 2006/0100677 A1 | 5/2006 | Blunnenkranz et al. |
| 2007/0027509 A1 | 2/2007 | Eisenberg et al. |

OTHER PUBLICATIONS

Final Office Action received for U.S. Appl. No. 11/523,159, dated Jun. 10, 2016, 6 pages.
Final Office Action received for U.S. Appl. No. 11/523,159, dated Mar. 25, 2016, 7 pages.
Final Office Action received for U.S. Appl. No. 11/523,159, dated Feb. 7, 2012, 8 pages.
Non-Final Office Action received for U.S. Appl. No. 11/523,159, dated May 13, 2011, 10 pages.
Non-Final Office Action received for U.S. Appl. No. 11/523,159 dated Nov. 5, 2015, 6 pages.
Non-Final Office Action received for U.S. Appl. No. 11/523,159, dated Mar. 30, 2017, 8 pages.

OPTICAL SWITCH AND METHOD FOR TREATMENT OF TISSUE

CROSS REFERENCE TO RELATED APPLICATION(S)

This application is a continuation of U.S. Ser. No. 11/523,159 filed on Sep. 18, 2006, which claims the benefit of priority, under 35 U.S.C. § 119(e), of U.S. Ser. No. 60/718,791 filed on Sep. 19, 2005. The content of both applications are hereby incorporated by reference in their entirety for all purposes.

BACKGROUND OF THE INVENTION

Field of the Invention

The present invention provides apparatus, method and system for photothermal treatment of retinal tissue.

Background

Conditions such as diabetic retinopathy and age-related macular degeneration are subject to photocoagulative treatment with laser light. While this type of laser light treatment slows the damage rate of the underlying disease, it has its set of problems. For example, because the treatment entails exposing the eye to a large number of laser light pulses for a long period of time (typically each pulse is on the order of 100 ms or more), damage can be caused to the patient's sensory retina from the heat that is generated. During the treatment, heat is generated predominantly in the retinal pigmented epithelium (RPE), which is the melanin-containing layer of the retina directly beneath the photoreceptors of the sensory retina. Although visible light is predominantly absorbed in the RPE, this type of treatment irreversibly damages the overlying sensory retina and negatively affects the patient's vision. Such long pulses are not required to perform effective treatment, and cause undue patient discomfort and tissue damage. However, most surgical laser systems available today utilize mechanical shutters that require milliseconds to open and close, thus limiting the lower limit of available pulse durations.

Because laser treatment often entails the use of long pulses that could potentially cause damage to the patient's sensory retina, the treatment is often performed with pulses of shorter duration. Turning the laser source on and off directly, however, is neither effective nor cost-efficient because of the optical transients generated and possible damage to the light source. Without the ability to shutter the beam downstream, using a chopper or rotating polygon scanner as a shutter element is not desirable. Because their reliable performance is based upon constant motion, such devices do not provide a convenient and efficient means to adjust the ultimate shape, size and location of the transmitted light.

Today either a slit-lamp-mounted laser delivery device or head mounted laser indirect ophthalmoscope are commonly used for this type of laser light treatment. In the slit lamp device, the slit lamp is arranged to allow easy illumination and microscopic viewing of the eye of a seated patient. Slit lamps used in laser treatment/surgery are a high-brightness forward illuminator and microscope assemblies mounted on a shared pivot point. This arrangement allows the viewing angle of the microscope and illuminator to be changed as often as desired without moving the field of illumination or visualization transversely.

While the most often-used of such devices, slit-lamp-mounted laser delivery devices have their shortcomings. Specifically, certain parts of the eye are difficult to treat with this type of device. For example, the anterior aspect of a retinal break is by far the most important part to seal, as this is the area most subjected to vitreous traction. However, this area is not completely accessible with a slit-lamp-delivered laser system. Also, the slit-lamp-mounted laser delivery device is not well suited for treating small infants or bed-ridden patients. Furthermore, it is difficult to orient the patient's head position with slit-lamp-mounted systems. Thus, these devices have limited ability to treat patients with detached retinas and other conditions where gas or dense fluids have been introduced into the eye to secure detached tissues prior to laser exposure. To treat these conditions, the patient's head is oriented to reposition the tissue or tamponade material.

The laser indirect ophthalmoscope (LIO) may be used in lieu of the slit-lamp-mounted laser delivery device to overcome these shortcomings. The LIO is worn on the physician's head and is used to treat peripheral retinal disorders, particularly in infants or adults requiring treatment in the supine position. It is typically used in an operating room or clinical environment. Traditionally, an LIO is used with a fiber optic to a beam delivery system that is worn by a physician to deliver treatment spots one at a time, with the physician moving their head and/or the objective lens to reposition the aiming beam prior to delivering another spot of treatment light.

An improved technique of pulsed laser treatment is desired. Both of the abovementioned approaches lend themselves to the use of the present invention.

SUMMARY OF THE INVENTION

A new system and method of pulsed laser treatment provides superior generation of pulsed light (e.g. for single or plural output devices).

An optical switch includes a light source for generating an optical beam, an aperture element having a light-transmitting portion and a light-blocking portion, and an optical element positionable to direct the optical beam to the aperture element, wherein the optical element is movable for translating the optical beam across the light-transmitting and light-blocking portions of the aperture element to produce one or more pulses of light from the optical beam.

A photomedical system for treating target tissue includes a light source for generating an optical beam, an aperture element having a light-transmitting portion and a light-blocking portion, an optical element positionable to direct the optical beam to the aperture element wherein the optical element is movable for translating the optical beam across the light-transmitting and light-blocking portions of the aperture element to produce one or more pulses of light from the optical beam, an optic for focusing the one or more pulses of the optical beam onto target tissue, and a controller for controlling movement of the optical element to produce the one or more pulses of light.

A photomedical system for treating target tissue can also include a plurality of light sources for generating a plurality of optical beams, an aperture element having a light-transmitting portion and a light-blocking portion, an optical element positionable to selectively direct the optical beams to the aperture element wherein the optical element is movable for translating the optical beams across the light-transmitting and light-blocking portions of the aperture element to produce one or more pulses of light from the optical beams, an optic for focusing the one or more pulses of the optical beams onto target tissue, and a controller for controlling movement of the optical element to produce the one or more pulses of light.

A method of treating target tissue includes generating an optical beam, translating the optical beam across an aperture element using a moving optical element to produce one or more pulses of light from the optical beam wherein the aperture element includes a light-transmitting portion and a light-blocking portion, and focusing the one or more pulses of the optical beam onto target tissue.

Other objects and features of the present invention will become apparent by a review of the specification, claims and appended figures.

DETAILED DESCRIPTION OF THE EMBODIMENTS

The present invention is based on the concept of generating optical pulses of arbitrary temporal profile by moving an optical beam relative to a fixed aperture element as part of an optical delivery device. Instead of making the light source "strobe" or using a simple shutter to generate a pulse, a light source is turned on continuously and the beam is moved across transparent and opaque portions of the aperture element so that it looks like the light is turned on and off from the other side of the aperture element. A robust, cost-effective, flexible, and efficient pulse delivery system can be made by implementing the moving beam and the fixed aperture element in an optical beam delivery device.

Figure 1:
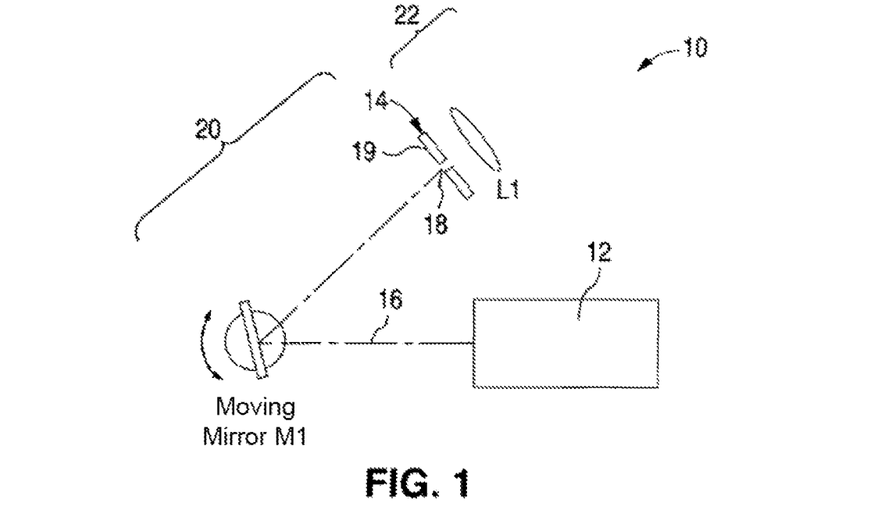
FIG. 1 is a schematic diagram of an optical switch.

FIG. 1 is a schematic diagram of an optical switch 10, which is configured as a pulse generator. The optical switch 10 includes a light source 12 (e.g. a laser device, a light emitting diode, etc.), a moving mirror M1, an aperture element 14, and a lens L1. The light source 12 outputs an optical beam 16. A non-limiting example can be a 2.5 Watt, 532 nm laser beam from a diode pumped solid state laser source. The mirror M1 is disposed on the input side 20 of the aperture element 14 and may be a galvanometer-mounted moving mirror that can be rotated to change the plane of the reflective surface and thus the direction of optical beam 16. The aperture element 14 has at least one light-transmitting portion 18 and at least one light-blocking portion 19. The light-transmitting portion 18 may be formed of a transparent solid material (e.g., glass, LCD cell, etc.) or of a physical void (i.e. an open aperture, etc.) formed in an opaque material. Using LCD (liquid crystal display) cells to create the light transmitting and blocking portions 18/19 has the advantage of allowing the size, shape and/or location of these portions to be dynamically adjusted. As an example, a lens L1 may be positioned on the output side 22 of the aperture element 14 (to receive the optical beam after it passes through the transmitting portion 18 of aperture element 14) and focuses the beam in any desired manner.

During operation, the optical beam 16 is aimed at the light-transmitting portion 18 or the light-blocking portion 19 depending on the position of the mirror M1. Thus, by rotating the mirror M1 rapidly back and forth within a prescribed range, the optical beam 16 is repeatedly translated across the light-transmitting portion 18 and the light-blocking portion 19, which generates a pulse effect on the distal side of the aperture element 14.

Figure 2:
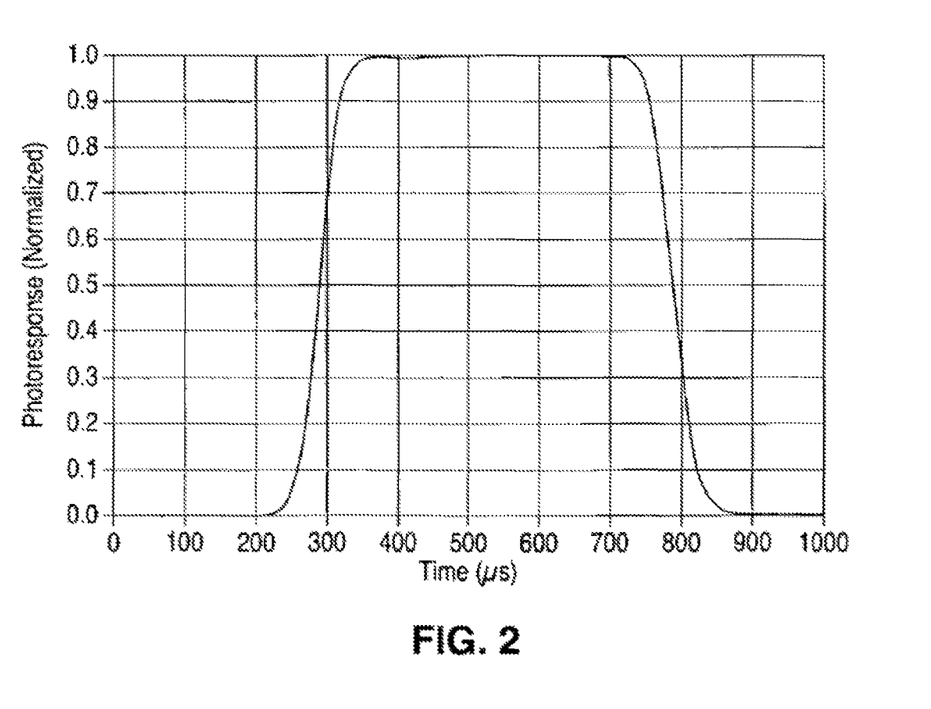
FIG. 2 is a plot showing the photoresponse of an optical beam down stream from the optical switch as a function of time.

FIG. 2 is a plot showing the normalized power of the optical beam 16 that passes through the aperture element 14 as a function of time, as the optical beam 16 is swept across the light transmitting portion 18 of the aperture element 14 by moving mirror M1. The exemplary plot has a pulse duration of about 500 µs. Pulses as short as 10 µs can be achieved. By doing so, the average power of the laser source is efficiently utilized to provide flexible and rapid ophthalmic therapy.

Figure 3:
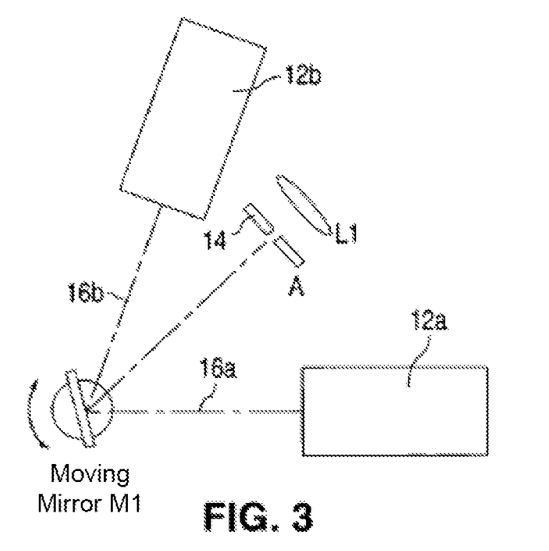
FIG. 3 is a schematic diagram of an additional embodiment of the optical switch.

FIG. 3 is a schematic diagram of another embodiment of the optical switch 10. The optical switch 10 of this embodiment is substantially similar to that of FIG. 1 except that there are two light sources 12a, 12b that generate two optical beams 16a, 16b. The two optical beams 16a, 16b may be of different wavelengths and/or intensities, and the two light sources 12a, 12b may be turned on and off independently at different times, depending on the particular needs of the procedure being performed.

Figure 4:
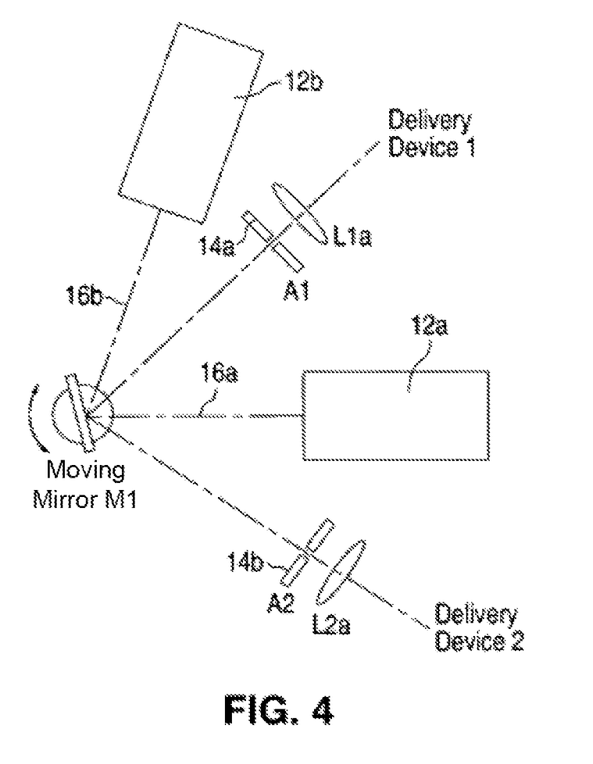
FIG. 4 is a schematic diagram of the optical switch in accordance with an embodiment that allows selection between different delivery modes.

FIG. 4 is a schematic diagram of the optical switch in accordance with an embodiment that allows selection between different delivery modes. Similar to the embodiment of FIG. 3, there are multiple light sources 12a, 12b generating optical beams 16a, 16b. However, unlike the embodiment of FIG. 3, there are two sets of aperture elements 14a, 14b, each aperture element 14a, 14b being optically coupled to a different delivery device (device 1 or device 2). By rotating the mirror M1, it sweeps the optical beams 16a/16b across one of the aperture elements 14a, 14b depending on which delivery device the user chooses, thus selectively producing pulsed light in either delivery device.

The configuration of FIG. 4 can be modified by eliminating the second light source 12, and using the resulting optical switch 10 to direct light from the light source 12a to a variety of different delivery devices. A photomedical system that uses the optical switch 10 in this manner could offer a selection of more than one therapeutic output port. For example, a user (e.g., a physician) could choose between slitlamp-based delivery device, and endoprobe, or an indirect ophthalmoscope delivery device depending upon the details of the patient's condition. The optical switch 10 could also be used to switch between different delivery devices during a single treatment, and provide pulsed light by translating the beam 16a across the appropriate aperture element 14a, 14b. For example, if a user wants to use more than one intraocular probe to perform retinal photocoagulation, the optical switch 10 allows the multiple probes to be inserted simultaneously.

Figure 5A:
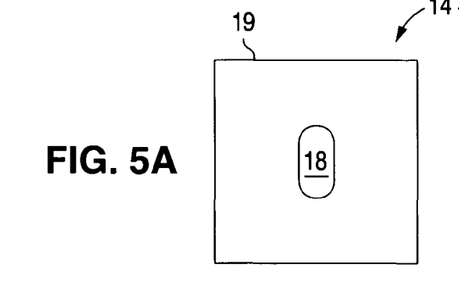
FIGS. 5A, 5B, 5C, and 5D are different embodiments of the aperture element 14 of the optical switch that can be used to shape or size the optical beam.
Figure 5B:
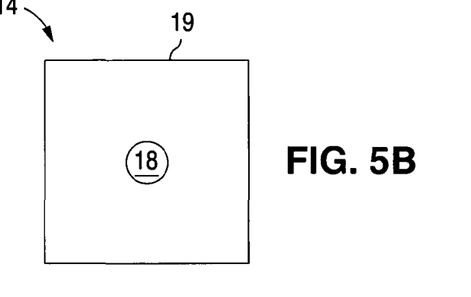
Figure 5C:
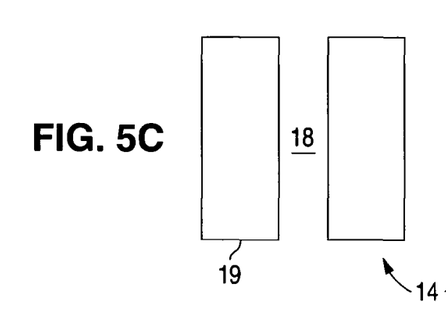
Figure 5D:
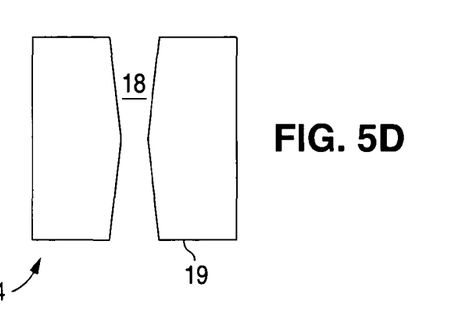

FIGS. 5A, 5B, 5C, and 5D are different embodiments of the aperture element 14 that can be used with the optical beam 16. In these Figures, the light-transmitting portion 18 is shown in white and the light-blocking portion 19 is shown in black. In FIG. 5A, the light-transmitting portion 18 has an elongated oval shape. In FIG. 5B, the light-transmitting portion 18 has a round shape. In FIG. 5C, the light-transmitting portion 18 has a rectangular slit shape. In FIG. 5D, the light-transmitting portion 18 has the shape of a slit with angled sides. The shapes of the light-transmitting portion 18 shown in these Figures are not limiting or exhaustive, and the shapes may be changed or adjusted according to the needs of a particular procedure. Not only can these shaped light-transmitting portions 18 be used to create pulsed light (i.e. by translating the beam across them, or changing the incident angle through them), but they can also be used to provide variable beam attenuation, temporal and spatial beam shaping, and beam re-sizing through proper selection of the shape and size of the light-transmitting portion 18 and/or through variable positioning of the beam relative thereto.

Figure 6:
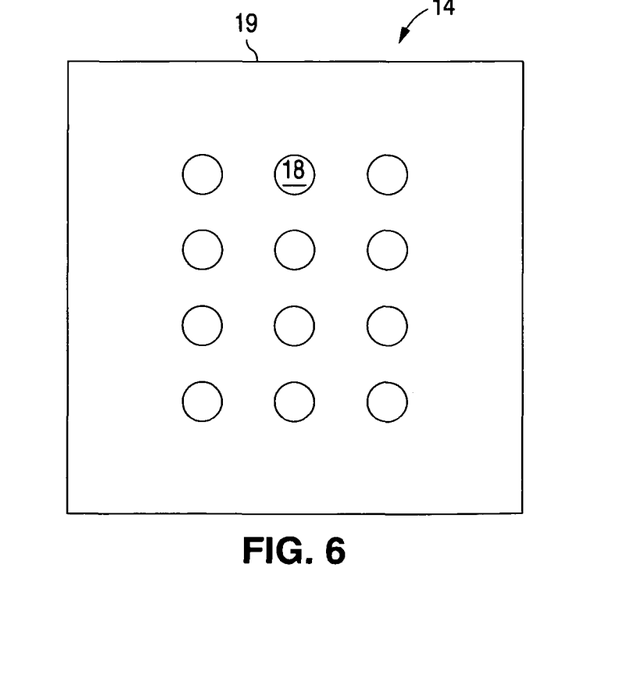
FIG. 6 is an embodiment of the aperture element 14 with multiple light-transmitting portions 18 to generate a pattern.

FIG. 6 is an embodiment of the aperture element 14 with multiple light-transmitting portions 18 to generate a pattern. Although the particular pattern is a two-dimensional 3×4 array of circular light-transmitting portions 18, the numbers, shapes and relative positioning of the light-transmitting portions 18 can vary. The beam can be translated across each of the light-transmitting portions 18 sequentially one at a time, or the beam size can be much larger than the spacings between portions 18 in which several or all of the light-transmitting portions 18 are illuminated simultaneously.

Figure 7A:
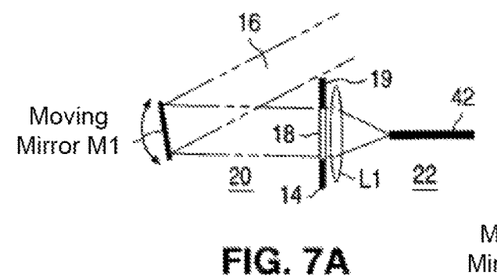
FIGS. 7A, 7B, 8A, 8B, 9A, 9B, 10A, and 10B show various configurations of the optical switch.
Figure 7B:
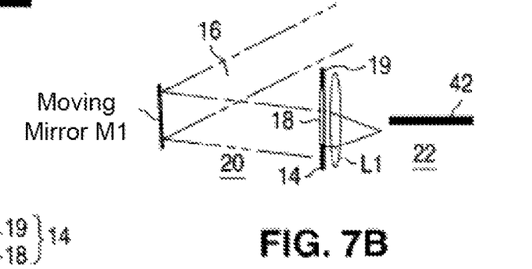

FIGS. 7A-10B show various other configurations of the optical switch 10. FIGS. 7A and 7B show a configuration of the optical switch 10 wherein a lens L1 is located on the output side 22 of the aperture element 14. In FIG. 7A, the moving mirror M1 is at an angle such that the optical beam 16 is reflected toward the light-transmitting portion 18 of the aperture element 14. More than a critical fraction (e.g., substantially all) of the optical beam 16 reaches the lens L1, which focuses the optical beam 16 into the input end of an optical fiber 42. The state in FIG. 7A represents the pulse being "on." If the moving mirror M1 rotates, the optical beam 16 is reflected so that some of it is directed toward the light-transmitting portion 18 but the rest of it is incident on the light-blocking portion 19, as shown in FIG. 7B. Under these conditions, the amount of optical beam 16 that enters the optical fiber 42 is significantly reduced (or eliminated) compared to the conditions in FIG. 7A. If less than the critical fraction of the optical beam is incident on the light-transmitting portion 18, the pulse is in an "off" state. The light is repeatedly turned on and off (i.e. pulse generation) by changing the position of the moving mirror M1. The pulse being "on" or "off" is described as viewed from the output side 22 of the aperture element 14. When used with optical fibers, the aperture element 14 could be an element separate from optical fiber 42, or could be incorporated as part of the optical connector at the end of the optical fiber 14. such as is shown in FIGS. 8A and 8b. The transmitting portion may also be the core of the optical fiber itself. When the fiber is used as the aperture, it must be noted that it accepts light only in its core, and only at a certain numerical aperture (NA). In this way, optical beam 16 may be switched on and off by moving it on the core, and/or by changing its incident angle.

Figure 8A:
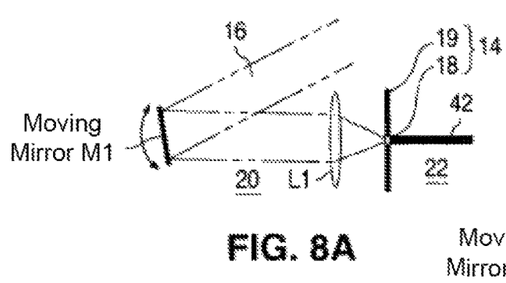
Figure 8B:
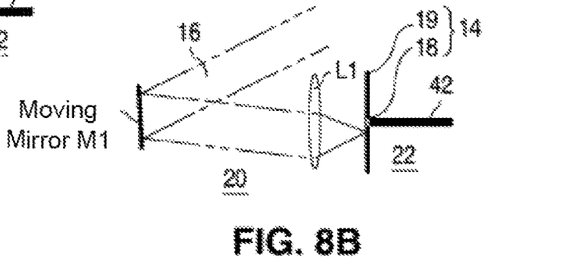

FIGS. 8A and 8B show a configuration of the optical switch 10 wherein the lens L1 is located on the input side 20 of the aperture element 14, between the moving mirror M1 and the aperture element 14. In FIG. 8A, the lens L1 focuses the optical beam 16 from the moving mirror M1 on the light-transmitting portion 18 of the aperture element 14. The optical fiber 42 is positioned close to the aperture element 14 so that substantially all of the optical beam 16 is coupled into the optical fiber 42. The state in FIG. 8A represents the pulse being "on" If the moving mirror M1 rotates, the optical beam 16 is directed to the lens L1 off-center so that the lens L1 focuses the beam on a light-blocking portion 19 of the aperture element 14, as shown in FIG. 8B. Under these conditions, the amount of optical beam 16 that enters the fiber unit 42 is significantly reduced (or eliminated) compared to the conditions in FIG. 8A. If less than the critical fraction of the optical beam is incident on the light-transmitting portion 18, then the pulse is in an "off" state. The light is repeatedly turned on and off (i.e. pulse generation) by changing the position of the moving mirror M1.

Figure 9A:
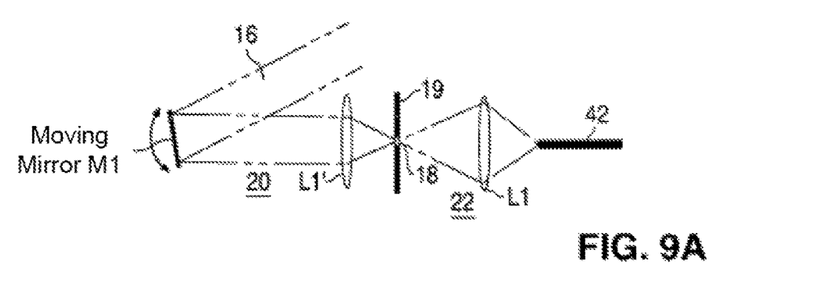
Figure 9B:
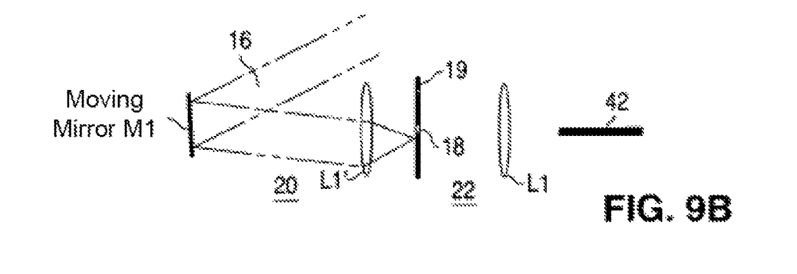

FIGS. 9A and 9B show a configuration of the optical switch 10 wherein the lens L1 is located on the output side 22 of the aperture element 14 and a lens L1' is located on the input side 20 between the moving mirror M1 and the aperture element 14. In FIG. 9A, the moving mirror M1 is at an angle such that the lens L1' focuses the optical beam 16 onto the light-transmitting portion 18 of the aperture element 14. The lens L1 is positioned such that its focal point lies in the light-transmitting portion 18 of the aperture element 14 and coincides with the focal point of the lens L1'. The lens L1 then focuses the optical beam 16 that passed through the aperture element 14 into the optical fiber 42. Since more than a critical fraction of the optical beam 16 is incident on the light-transmitting portion 18, the state in FIG. 9A represents the pulse being "on" If the moving mirror M1 is rotated, the lens L1' focuses the optical beam 16 on the light-blocking portion 19, as shown in FIG. 9B. Under these conditions, less than the critical fraction of the optical beam passes through the aperture element 14, and the pulse is in an "off" state. The light is repeatedly turned on and off (i.e. pulse generation) by changing the position of the moving mirror M1. With the use of an extra lens L1' on the input side 20, the light-transmitting portion 18 of the aperture element 14 may be made much smaller than in the case where there is no lens L1'. (e.g., in FIG. 7A and FIG. 7B) because the light is focused to a very small diameter at the aperture element 14 while its angular velocity is increased. This combination yields amplified switching speeds.

Figure 10A:
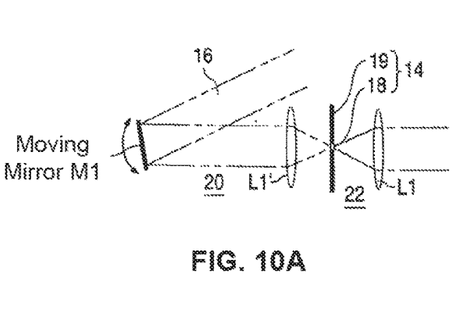
Figure 10B:
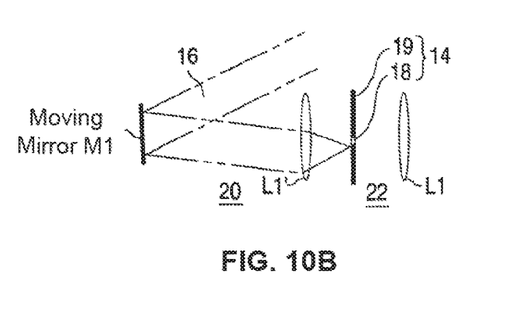

FIGS. 10A and 10B show a configuration of the optical switch 10 similar to that of FIGS. 9A and 9B, except there is no optical fiber and lens L1 is positioned to collimate the light pulses. The embodiment of FIGS. 10A and 10B is suitable for photomedical systems that do not use an optical fiber delivery system, but instead allow free-space propagation of the optical beam 16.

Figure 11:
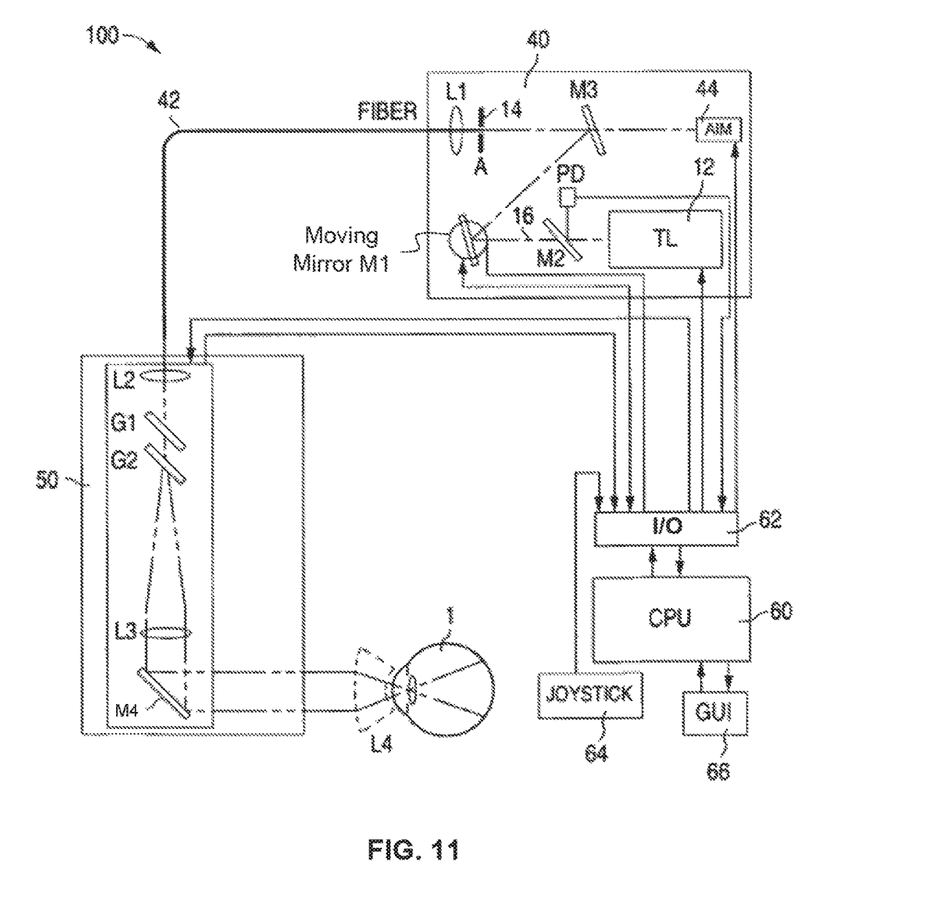
FIG. 11 is a schematic diagram of a photomedical system that incorporates the optical switch.

FIG. 11 is a schematic diagram of a photomedical system 100 that utilizes optical switch 10. As shown, the photomedical system 100 includes a light generation unit 40 and a pattern generation unit 50 that are optically coupled to each other through an optical fiber 42. The photomedical system 100 also includes a CPU 60, an input/output device 62, a graphic user interface 66 and a secondary input unit 64. The CPU 60 controls the light generation unit 40 and the pattern generation unit 50 via the input/output device 62. The CPU 60 may be a microprocessor, microcontroller, or any other type of suitable control electronics (i.e. controller).

The light generation unit 40 includes the optical switch 10, (shown with the embodiment of FIG. 3). The light source 12 is controlled by CPU 60 via the input and output (I/O) device 62 to generate the optical beam 16, whose centerline is shown by dashed lines. The optical beam 16, upon being generated by the light source 12, encounters the mirror M2 which directs a portion of the optical beam 16 to a photodiode PD1. The photodiode PD1 serves to sample and measure the power of the light for safety purposes. The photodiode PD1 may be replaced with other types of sensors, as appropriate. The portion of the light from the mirror M2 that is not directed to the photodiode PD1 reaches the moving mirror M1, which is described above. The optical beam 16 is reflected by the mirror M1 toward the aperture element 14. In the particular embodiment that is shown, optional mirror M3 is used to redirect the optical beam 16 before it reaches the aperture element 14. The lens L1, which is on the output side 22 of the aperture element 14, focuses any of the optical beam 16 that passed through the aperture element 14 into the optical fiber 42. Pulsed light is delivered to the optical fiber by translating the optical beam across the aperture element 14 using movable mirror M1.

An optional aiming beam source 44 may be incorporated into the light generation unit 40 to provide an aiming optical beam that helps the user aim the treatment beam 16 before and/or during treatment. This additional beam could also, or instead, be used to "fixate" the patient's gaze during the treatment. The aiming/fixation beam generated by the beam source 44 utilizes the same optical path as the optical beam 16 by passing through mirror M3 and being delivered through the optical fiber 42.

The pattern generation unit 50 receives the optical beam 16 from optical fiber 42. Lenses L2, L3 and mirror M4 of the pattern generation unit 50 function to direct the optical beam 16 to a target object 1, which in this case is the retina of the patient. Light exiting the optical fiber 42 first encounters lens L2 and becomes collimated. The collimated optical beam goes through a pair of moving mirrors Gi, G2 that produce a desired pattern of light using the optical beam 16 by either spatially dividing the optical beam 16 into multiple beams or translating (i.e., temporally dividing) the optical beam 16 in a desired pattern. Preferably, mirrors G1, G2 are galvo mounted mirrors that rotate in two orthogonal directions relative to each other. The optical beams arranged in the desired pattern enter the lens L3, which images the optical midpoint of the moving mirrors G1, G2 onto the mirror M4 to minimize the size of the mirror M4 in an attempt to position it more centrally in the binocular viewing path of the slit lamp biomicroscope.

In some embodiments, the pattern generation unit 50 may incorporate a zooming lens (not shown). The zooming lens (e.g. a single lens or a compound lens) is configured for adjusting the intrinsic size of the pattern or the elements that form the pattern. The zooming lens allows easy adjustment of the size of the light pattern on the target object 1, and may be controlled by the CPU 12.

An ophthalmic lens L4 may be placed close to the target object 1 to focus the light pattern on the target object 1. A user (e.g., a physician) controls various aspects of the photomedical system 100 (e.g., pulse duration, zoom level of the projected pattern, treatment activation) by using a user interface unit, which may include one or more input units 64 (e.g., joystick, keyboard, keypad, knob, footswitch, etc.) and the graphic user interface 66.

Figure 12:
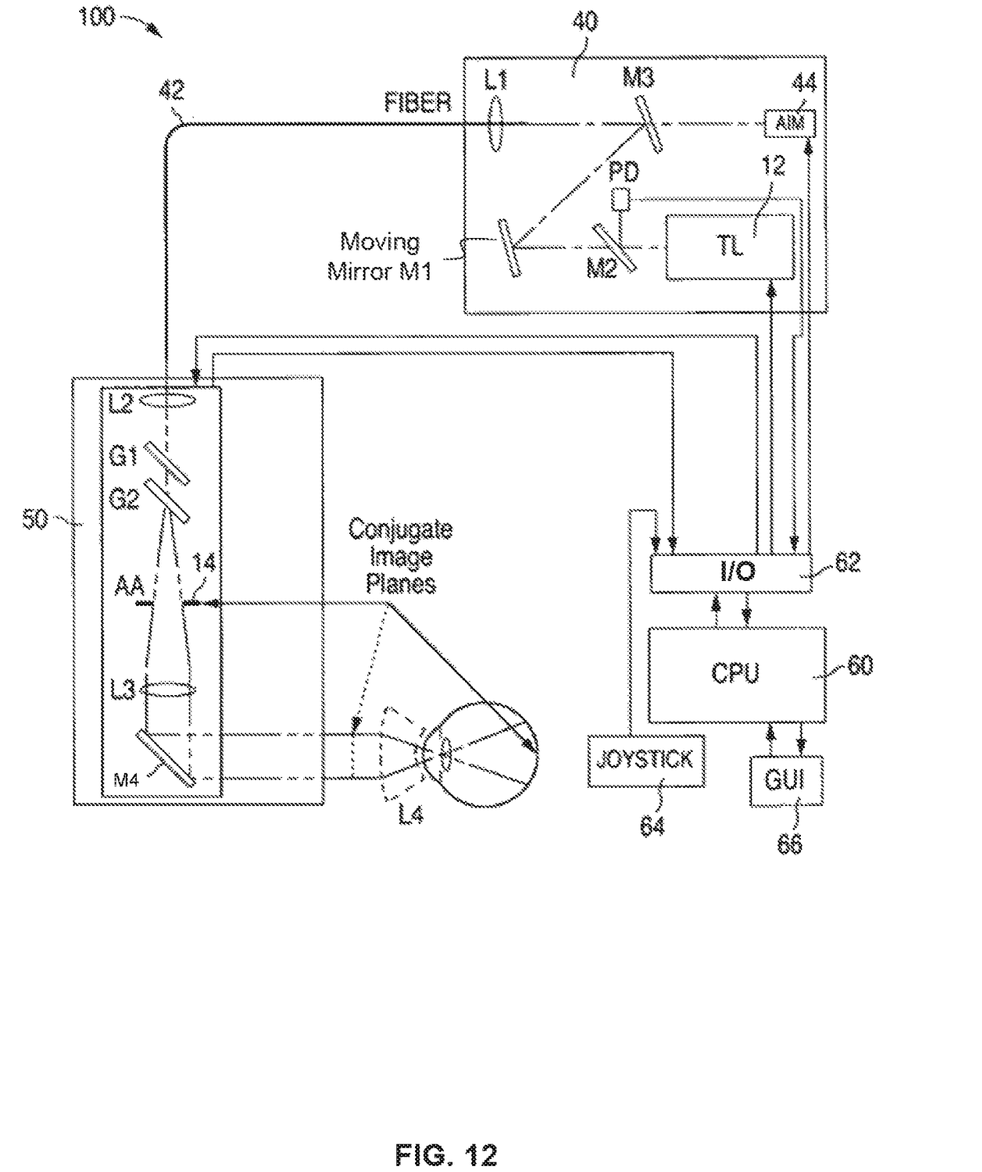
FIG. 12 is a schematic diagram of an alternate embodiment of the photomedical system that incorporates the optical switch.

FIG. 12 is an embodiment of the photomedical system 100 similar to that shown in FIG. 11, with a main difference being the incorporation of the aperture element 14 into the pattern generation unit 50 instead of the light generation unit 40. In this embodiment, the aperture element 14 is positioned between the set of moving mirrors G1, G2 and the lens L3. The moving mirrors G1, G2 move the optical beam 16 across the aperture element 14 in substantially the same manner as was done by moving mirror M1 of FIG. 1. Thus, depending on whether the translating beam hits a light-transmitting portion 18 or a light-blocking portion 19, the optical beam 16 is turned on and off and reaches the target object 1 as one or more pulses.

In all the above embodiments, aperture element 14 may be a static element, or it can be dynamically rewritable. For example, the aperture element 14 may be a liquid crystal display (LCD) panel, that can vary the light-transmitting portion 18 and light-blocking portion 19 during treatment or in-between separate treatments. In the systems of FIGS. 11 and 12, the CPU 60 can control the shape, size, and/or arrangement of the light-transmitting portions 18 in response to user instructions input through the input unit 64.

Although the invention has been described with reference to the above examples, it will be understood that modifications and variations are encompassed within the spirit and scope of the invention. For example, M1 can be replaced in the above embodiments with any movable optical element that translates the beam across the aperture element 14 through reflection or refraction, such as a rotating or translating prism or optical wedge, or a tilting or translating lens, etc. Accordingly, the invention is limited only by the following claims.

What is claimed is:

1. A method of treating target tissue using a photomedical system having a treatment light source, an aperture element having a liquid-crystal display (LCD) panel, an optical element, an optic, one or more input devices, and a controller, the method comprising:
  generating an optical treatment beam using the treatment light source;
  translating, using the optical element, at least the center of the optical treatment beam in a first direction across light-transmitting and light-blocking portions of the aperture element and in a second direction opposite the first direction across the light-transmitting and light-blocking portions of the first aperture element to generate a first plurality of pulses of light from the optical treatment beam, wherein LCD panel of the aperture element forms the light-transmitting portion and the light-blocking portion of the aperture element;
  focusing the first plurality of pulses of light onto the target tissue using the optic;
  after focusing the first plurality of pulses of light onto the target tissue, receiving one or more user inputs from the one or more input devices;
  adjusting, using the controller, a size of the light-transmitting portion and a size of the light-blocking portion, wherein the size of the light-transmitting portion and the size of the light-blocking portion are adjusted based on the one or more user inputs;
  translating, using the optical element, at least the center of the optical treatment beam in the first direction across the adjusted light-transmitting and light-blocking portions of the aperture element and in the second direction across the adjusted light-transmitting and light-blocking portions of the aperture element to generate a second plurality of pulses of light from the optical treatment beam; and
  focusing the second plurality of pulses of light onto the target tissue using the optic.

2. The method of claim 1, wherein each pulse of light of the second plurality of pulses of light strikes the target tissue for a longer duration of time than each pulse of light of the first plurality of pulses of light.

3. The method of claim 1, wherein each pulse of light of the second plurality of pulses of light strikes the target tissue for a shorter duration of time than each pulse of light of the first plurality of pulses of light.

4. The method of claim 1, wherein a size of each pulse of light of the second plurality of pulses of light is different than a size of each pulse of light of the first plurality of pulses of light.

5. The method of claim 1, wherein adjusting the size of the light-transmitting portion and the size of the light-blocking portion includes adjusting a shape of the light-transmitting portion and a shape of the light-blocking portion.

6. The method of claim 5, wherein a shape of each pulse of light of the second plurality of pulses of light is different than a shape of each pulse of light of the first plurality of pulses of light.

7. The method of claim 1, further comprising:
adjusting, using the controller, a location of the light-transmitting portion and a location of the light-blocking portion, wherein the location of the light-transmitting portion and the location of the light-blocking portion are adjusted based on the one or more user inputs.

8. The method of claim 1, wherein the light-transmitting portion of the aperture element includes a plurality of discrete light-transmitting spots, and wherein adjusting the size of the light-transmitting portion of the aperture element includes adjusting a size of one or more discrete light-transmitting spots of the plurality of discrete light-transmitting spots.

9. The method of claim 8, wherein adjusting the size of the one or more discrete light-transmitting spots includes adjusting a number of discrete light-transmitting spots included in the plurality of discrete light-transmitting spots.

10. The method of claim 8, further comprising:
adjusting, using the controller, a location of one or more discrete light-transmitting spots of the plurality of discrete light-transmitting spots, wherein the location of the one or more discrete light-transmitting spots is adjusted based on the one or more user inputs.

11. The method of claim 1, wherein the photomedical system further includes a pattern generation unit, further comprising:
generating, using the pattern generation unit, a pattern of the first plurality of pulses of light before focusing the first plurality of pulses of light onto the target tissue; and
generating, using the pattern generation unit, a pattern of the second plurality of pulses of light before focusing the second plurality of pulses of light onto the target tissue.

12. The method of claim 1, wherein the aperture element is stationary when the optical element is moving.

13. A photomedical system for treating target tissue of an eye, comprising:
a treatment light source for generating an optical treatment beam;
an aperture element having a liquid-crystal display (LCD) panel, wherein the LCD panel forms a light-transmitting portion of the aperture element and a light-blocking portion of the aperture element;
an optical element positionable to direct the optical treatment beam to the aperture element;
an optic;
one or more input devices; and
a controller configured to:
cause movement of the optical element to translate at least the center of the optical treatment beam in a first direction across the light-transmitting and light-blocking portions of the aperture element and in a second direction opposite the first direction across the light-transmitting and light-blocking portions of the aperture element to generate a first plurality of pulses of light from the optical treatment beam, wherein the optic focuses the first plurality of pulses of light onto target tissue;
after the first plurality of pulses of light are focused onto target tissue, receive one or more user inputs from the one or more input devices;
cause the LCD panel to adjust a size of the light-transmitting portion and a size of the light-blocking portion, wherein the size of the light-transmitting portion and the size of the light-blocking portion are adjusted based on the one or more user inputs; and
cause movement of the optical element to translate at least the center of the optical treatment beam in the first direction across the adjusted light-transmitting and light-blocking portions of the aperture element and in the second direction opposite the first direction across the adjusted light-transmitting and light-blocking portions of the aperture element to generate a second plurality of pulses of light from the optical treatment beam, wherein the optic focuses the second plurality of pulses of light onto target tissue.

14. The photomedical system of claim 13, wherein each pulse of light of the second plurality of pulses of light strikes the target tissue for a longer duration of time than each pulse of light of the first plurality of pulses of light.

15. The photomedical system of claim 13, wherein each pulse of light of the second plurality of pulses of light strikes the target tissue for a shorter duration of time than each pulse of light of the first plurality of pulses of light.

16. The photomedical system of claim 13, wherein a size of each pulse of light of the second plurality of pulses of light is different than a size of each pulse of light of the first plurality of pulses of light.

17. The photomedical system of claim 13, wherein causing the LCD panel to adjust the size of the light-transmitting portion and the size of the light-blocking portion includes causing the LCD panel to adjust a shape of the light-transmitting portion and a shape of the light-blocking portion.

18. The photomedical system of claim 17, wherein a shape of each pulse of light of the second plurality of pulses of light is different than a shape of each pulse of light of the first plurality of pulses of light.

19. The photomedical system of claim 13, wherein the controller is further configured to:
cause the LCD panel to adjust a location of the light-transmitting portion and a location of the light-blocking portion, wherein the location of the light-transmitting portion and the location of the light-blocking portion are adjusted based on the one or more user inputs.

20. The photomedical system of claim 13, wherein the light-transmitting portion of the aperture element includes a plurality of discrete light-transmitting spots, and wherein causing the LCD panel to adjust the size of the light-transmitting portion of the aperture element includes causing the LCD panel to adjust a size of one or more discrete light-transmitting spots of the plurality of discrete light-transmitting spots.

21. The photomedical system of claim 20, wherein causing the LCD panel to adjust the size of the one or more discrete light-transmitting spots includes causing the LCD panel to adjust a number of discrete light-transmitting spots included in the plurality of discrete light-transmitting spots.

22. The photomedical system of claim 20, wherein the controller is further configured to:
   cause the LCD panel to adjust a location of one or more discrete light-transmitting spots of the plurality of discrete light-transmitting spots, wherein the location of the one or more discrete light-transmitting spots is adjusted based on the one or more user inputs.

23. The photomedical system of claim 13, further comprising a pattern generation unit, wherein the pattern generation unit is configured to:
   generate a pattern of the first plurality of pulses of light before focusing the first plurality of pulses of light onto the target tissue; and
   generate a pattern of the second plurality of pulses of light before focusing the second plurality of pulses of light onto the target tissue.

24. The photomedical system of claim 13, wherein the aperture element is stationary when the optical element is moving.

* * * * *